(12) United States Patent
List et al.

(10) Patent No.: US 8,703,940 B2
(45) Date of Patent: Apr. 22, 2014

(54) PROCESS FOR PREPARING 3,6-DIHYDRO-1,3,5-TRIAZINE DERIVATIVES

(75) Inventors: Benjamin List, Mülheim an der Ruhr (DE); Xu Cheng, West Lafayette, IN (US)

(73) Assignee: Studiengesellschaft Kohle mbH, Mülheim an der Ruhr (DE)

( * ) Notice: Subject to any disclaimer, the term of this patent is extended or adjusted under 35 U.S.C. 154(b) by 730 days.

(21) Appl. No.: 12/742,286

(22) PCT Filed: Nov. 12, 2008

(86) PCT No.: PCT/DE2008/001858
§ 371 (c)(1),
(2), (4) Date: May 11, 2010

(87) PCT Pub. No.: WO2009/062483
PCT Pub. Date: May 22, 2009

(65) Prior Publication Data
US 2010/0256368 A1    Oct. 7, 2010

(30) Foreign Application Priority Data

Nov. 13, 2007 (DE) .......................... 10 2007 054 416

(51) Int. Cl.
*C07D 251/18* (2006.01)

(52) U.S. Cl.
USPC .......................... 544/204; 544/205

(58) Field of Classification Search
USPC ................... 544/204, 205
See application file for complete search history.

(56) References Cited

U.S. PATENT DOCUMENTS

| 2,251,234 A | * | 7/1941 | Swain ............................ 521/28 |
| 2,500,113 A | | 3/1950 | Banks et al. |
| 3,287,366 A | | 11/1966 | Newman et al. |

FOREIGN PATENT DOCUMENTS

| EP | 1 574 503 | 11/2005 |
| JP | 48 064088 | 9/1973 |
| JP | 54 014986 | 2/1979 |
| WO | 99 31088 | 6/1999 |
| WO | 01 55122 | 8/2001 |

* cited by examiner

*Primary Examiner* — James O Wilson
*Assistant Examiner* — Ebenezer O Sackey
(74) *Attorney, Agent, or Firm* — Norris McLaughlin & Marcus, P.A.

(57) ABSTRACT

A process for the synthesis of 3,6-dihydro-1,3,5-triazine derivatives is claimed wherein a biguanid is reacted with acetaldehyde in the presence of an inorganic and/or organic base. The process can be carried out at mild and therefore economical reaction conditions.

11 Claims, No Drawings

PROCESS FOR PREPARING 3,6-DIHYDRO-1,3,5-TRIAZINE DERIVATIVES

This application is a 371 of PCT/DE2008/001858 filed Nov. 12, 2008, which claims foreign priority benefit under 35 U.S.C. §119 of the German Patent Application No. 10 2007 054 416.4 filed Nov. 13, 2007.

The present invention relates to a process for the preparation of 3,6-dihydro-1,3,5-triazine derivatives, wherein a biguanide is reacted with an acetaldehyde in the presence of an inorganic and/or organic base.

3,6-Dihydro-1,3,5-triazine derivatives show pharmacological properties in the treatment of pathological conditions associated with the insulin-resistance syndrome. Several patents describe the preparation of 3,6-dihydro-1,3,5-triazine derivatives. For example, in U.S. Pat. No. 3,287,366 the synthesis of dihydro-triazine bearing the following structure is described:

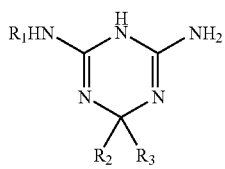

The synthesis involves the reaction of a mono-substituted bisguanidine and an aldehyde or ketone in presence of an acid at elevated temperatures.

Japanese patent JP48064088 describes the synthesis of dihydro-triazines bearing the following structure:

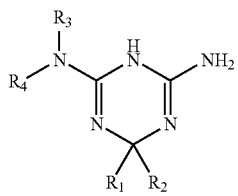

The analogous synthesis also involves heating under acidic condition.

Japanese patent JP54014986 describes the synthesis of dihydro-triazines bearing the following structure:

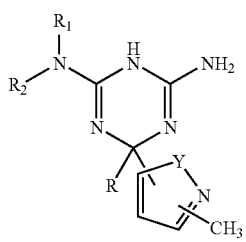

Similarly, this method requires heating under acidic conditions.

Patent application WO 01/55122 describes the synthesis of dihydro-triazines of the following structure:

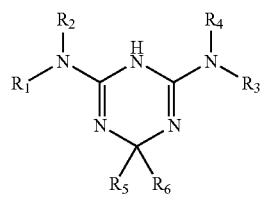

The synthesis is directed to the reaction of mono-substituted bisguanidines and an acetal, hemiacetal, ketal, hemiketal, aldehyde, or ketone in presence of an acid at elevated temperatures.

Common to the published procedures is the requirement of elevated temperature, which may require refluxing conditions or high pressure if low boiling point starting materials are employed as well as the use of an acid The invention had the object of finding a reaction at room temperature under normal pressure and without reflux conditions while only inexpensive starting materials are used. This would save energy and improve the safety of the process.

Unexpectedly, it has been found, that compounds of formula I can be prepared in presence of a base at room temperature under ambient pressure.

The invention relates to a process for the preparation of compounds of the formula I

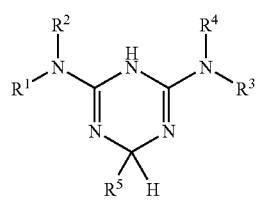

I in which
$R^1$, $R^2$, $R^3$ and $R^4$ are chosen independently from the following groups:

H;

$C_1$-$C_{20}$-alkyl optionally substituted by halogen, $C_1$-$C_5$-alkyl, $C_1$-$C_5$-alkoxy or $C_3$-$C_8$-cycloalkyl;

$C_2$-$C_{20}$-alkenyl optionally substituted by halogen, $C_1$-$C_5$-alkyl or $C_1$-$C_5$-alkoxy; $C_2$-$C_{20}$-alkynyl optionally substituted by halogen, $C_1$-$C_5$-alkyl or $C_1$-$C_5$-alkoxy; $C_3$-$C_8$-cycloalkyl optionally substituted by $C_1$-$C_5$-alkyl or $C_1$-$C_5$-alkoxy; $C_3$-$C_8$-heterocycloalkyl having one or more hetero atoms chosen from N, O and S and optionally substituted by $C_1$-$C_5$-alkyl or $C_1$-$C_5$-alkoxy;

$C_6$-$C_{14}$-aryl-($C_1$-$C_{20}$)alkyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl, $C_1$-$C_5$-alkoxy, cyano, trifluoromethyl, carboxyl, carboxymethyl or carboxyethyl;

$C_6$-$C_{14}$-aryl optionally substituted by amino, hydroxyl, thio, halogen, $C_1$-$C_5$-alkyl, $C_1$-$C_5$-alkoxy;

$C_1$-$C_{13}$-heteroaryl having one or more hetero atoms chosen from N, O and S and optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$R^1$ and $R^2$, on the one hand, and $R^3$ and $R^4$, on the other hand, possibly forming with the nitrogen atom an n-membered ring (n between 3 and 8) optionally comprising one or more hetero atoms chosen from N, O and S and possibly being substituted by one of the following groups: amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$R^5$ is chosen from the following groups:

$C_1$-$C_{20}$-alkyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$-)-alkoxy, cyano, trifluoromethyl, carboxyl, carboxymethyl or carboxyethyl;

$C_2$-$C_{20}$-alkenyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_2$-$C_{20}$-alkynyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_3$-$C_8$-cycloalkyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_3$-$C_8$-heterocycloalkyl having one or more hetero atoms chosen from N, O and S and optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_6$-$C_{14}$-aryl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_1$-$C_{13}$-heteroaryl having one or more hetero atoms chosen from N, O and S and optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_6$-$C_{14}$-aryl-($C_1$-$C_5$)-alkyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl, and pharmaceutically usable derivatives, solvates, salts and stereoisomers thereof, characterised in that a compound of the formula II

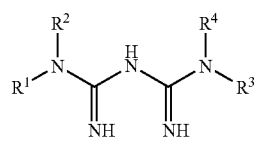

II in which $R^1$, $R^2$, $R^3$, $R^4$ are as defined above, is reacted with a compound of the formula III $R^5$—CHO

III in which $R^5$ is as defined above, in a polar solvent or solvant mixture in presence of an anorganic and/or organic base.

The base may be chosen from inorganic bases such as alkali hydroxides, alkali carbonates and alkali alcoholates, for example lithium hydroxide, sodium hydroxide, potassium hydroxide, sodium carbonate, potassium carbonate, sodium methanolate, sodium ethanolate, etc. or organic bases such as triethyl amine, diisopropylethyl amine, pyridine, pyrrol, pyrrolidine, piperidine, etc. and any mixtures of the above. With regard to the yield good results may be obtained with strong basids, in particular alkali hydroxides etc., whereas sodium hydroxide is preferred.

The process can be carried out in a solvent. Preferably, this is used in an amount that the reaction mixture can be stirred. The solvent may be chosen from from a wide variety of solvents which does not affect the reaction adversely such as Water, methanol, ethanol, isopropanol, n-butanol, 2-butanol, i-butanol, t-butanol and N,N-dimethyl formamide etc. or any mixtures of the solvents mentioned. Particularly suitable solvents are water, alcohols and mixtures of water and alcohols, such as a mixture of water and methanol.

For carrying out the reaction it is advantageous in case the compound of the formula II and of the formula III are present in equimolar amounts up to an excess of the compounds of the formula III based on the compound with the formula II. In a preferred embodiment, the concentration of the compound of formula III ranges from 1 equivalent to 10 equivalents to the compound of formula II.

The amount of base added may vary in wide ranges. Preferably, the amount of the base ranges from 0.5 equivalents to 10 equivalents, particular from 0.8 to 2 equivalents, with reference to the compound of the formula II. In a preferred embodiment, the base is used in equimolar amounts with reference to the compound of formula II.

The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds according to the invention and so-called prodrug compounds. The term "prodrug derivatives" is taken to mean compounds of the formula I which have been modified with, for example, alkyl or acyl groups, sugars or oligopeptides and which are rapidly cleaved in the organism to form the active compounds according to the invention. These also include biodegradable polymer derivatives of the compounds according to the invention, as described, for example, in Int. J. Pharm. 115, 61-67 (1995).

Isomers of the compounds of formula I are intend to mean the stereoisomers and the tautomers.

The inventive reaction has the advantageous that it can be carried out at ambient pressure. The reaction temperature may vary from temperatures of −10° C. up to temperatures of 100° C. In preferred embodiment the reaction is carried out at room temperature. In case weak bases are used, it may be advantageous to carry out the reaction at higher temperatures.

For all radicals which occur more than once, such as, for example, alkyl or optional substituents on aryl or heterocyclic residues, their meanings are independent of one another.

Alkyl is unbranched (linear) or branched, and has 1, 2, 3, 4, 5, 6, 7, 8, 9, 10, 11, 12, 13, 14, 15, 16, 17, 18, 19 or 20 carbon atoms. Alkyl is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, -ethyl-2-methylpropyl, 1,1,2- or 1,2,2-trimethylpropyl, furthermore preferably, for example, trifluoromethyl.

Alkyl is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl is preferably cyclopropyl, cyclobutyl, cyclopentyl, cyclohexyl or cycloheptyl. Alkylene is preferably methylene, ethylene, propylene, butylene, pentylene or hexylene, furthermore branched alkylene.

Alkenyl is preferably vinyl.

Alkynyl is preferably C≡CH.

Halogen is F, Cl, Br or I.

Alkoxy is preferably methoxy, ethoxy, propoxy or butoxy.

$C_3$-$C_8$-Heterocycloalkyl having one or more hetero atoms chosen from N, O and S preferably is 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted is meant to be unsubstituted or mono-, di-, tri-, tetra- or pentasubstituted.

Aryl preferably is phenyl, naphthyl or biphenyl.

Aryl alkyl preferably is benzyl.

Heteroaryl having one or more hetero atoms chosen from N, O and S preferably is 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

$R^1$, $R^2$, $R^3$ and $R^4$ preferably are chosen independently from the following groups:

$C_1$-$C_{20}$-alkyl optionally substituted by halogen, $C_1$-$C_5$-alkyl, $C_1$-$C_5$-alkoxy or $C_3$-$C_8$-cycloalkyl;

$C_2$-$C_{20}$-alkenyl optionally substituted by halogen, $C_1$-$C_5$-alkyl or $C_1$-$C_5$-alkoxy;

$C_2$-$C_{20}$-alkynyl optionally substituted by halogen, $C_1$-$C_5$-alkyl or $C_1$-$C_5$-alkoxy;

$C_3$-$C_8$-cycloalkyl optionally substituted by $C_1$-$C_5$-alkyl or $C_1$-$C_5$-alkoxy;

$C_3$-$C_8$-heterocycloalkyl having one or more hetero atoms chosen from N, O and S and optionally substituted by $C_1$-$C_5$-alkyl or $C_1$-$C_5$-alkoxy;

$C_6$-$C_{14}$-aryl-($C_1$-$C_{20}$)-alkyl optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$C_6$-$C_{14}$-aryl optionally substituted by amino, hydroxyl, thio, halogen, $C_1$-$C_5$-alkyl, $C_1$-$C_5$-alkoxy;

$C_1$-$C_{13}$-heteroaryl having one or more hetero atoms chosen from N, O and S and optionally substituted by amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$R^1$ and $R^2$, on the one hand, and $R^3$ and $R^4$, on the other hand, possibly forming with the nitrogen atom an n-membered ring (n between 3 and 8) optionally comprising one or more hetero atoms chosen from N, O and S and possibly being substituted by one of the following groups: amino, hydroxyl, thio, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl.

A preferred process for the preparation of compounds of formula I is related to compounds in which $R^1$, $R^2$ are independently from each other $C_1$-$C_{20}$-alkyl;

$R^3$, $R^4$ are H;

$R^5$ is $C_1$-$C_{20}$-alkyl.

A particularly preferred process for the preparation of compounds of formula I is related to compounds in which $R^1$, $R^2$ are independently from each other $C_1$-$C_5$-alkyl;

$R^3$, $R^4$ are H;

$R^5$ is $C_1$-$C_6$-alkyl.

Most particularly preferred is a process for the preparation of a compound of formula I in which $R^1$, $R^2$ are methyl;

$R^3$, $R^4$ are H;

$R^5$ is methyl.

There is an example giving further detail on the invention, but the invention is not limited within the example.

EXAMPLE 1

Preparation of 2-amino-3,6-dihydro-4-dimethylamino-6-methyl-1,3,5-triazine

A 4 L two neck flask charged with 662 g (4 mol) metformin HCl and 1600 mL MeOH was stirred with a magnetic bar at 750 rpm at room temperature with a water bath. To this suspension was added sodium hydroxide 160 g (4 mol) in 200 mL water through one dropping funnel. At the same time acetaldehyde 226 mL (4 mol) in 400 mL of MeOH in another funnel was added to the mixture. The addition of NaOH solution finished in 70 minutes whereas the addition of acetaldehyde finished in 100 minutes. Then, the reaction mixture was filtered through celite to remove the sodium chloride. The solution was concentrated to give a white solid that was extracted with 1.2 L of hot ethanol to give a suspension. After filtration, the ethanol solution was concentrated to give a pale yellow solid, 520 g, yield is 84%.

$^1$H NMR (300 MHz, CDCl$_3$) δ 1.37 (d, J=6.0 Hz, 3H), 2.98 (s, 6H), 3.46 (s, 1H), 4.83 (q, J=6.0 Hz, 1H). $^{13}$C NMR (300 MHz, CDCl$_3$) δ 24.5, 36.4, 63.0.

EXAMPLE 2

To a suspension of metfomin HCl 1.65 g (10 mmol) and sodium hydroxide 0.4 g (10 mmol) on 10 mL methanol was added a solution of acetaldehyde 0.56 mL (10 mmol) in 4 mL methanol at room temperature during 10 minutes, followed by stirring for 1 hour. Then the solution was filtered and concentrated to give white solid. The white solid was dissolved in 10 mL hot ethanol and filtered again. After concentration under vacuum, 1.4 g white solid with obtained, yield: 90%.

EXAMPLE 3

To a solution of metformin HCl 1.65 g (10 mmol) and sodium hydroxide 0.4 g (10 mmol) in 10 mL water was added a solution of acetaldehyde 0.56 mL (10 mmol) in 4 mL water during 10 minutes. After 1 hour at room temperature. The solution was concentrated to give white solid. Then the solid was dissolved in 10 mL ethanol and filtered. After concentration, 1.45 g white solid was achieved, yield 93%.

The invention claimed is:
1. A process for preparing a compound of formula I:

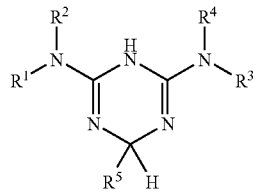

I in which
$R^1$, $R^2$, $R^3$ and $R^4$ are chosen independently from the following groups:
H;
$C_1$-$C_{20}$-alkyl optionally substituted by halogen, $C_1$-$C_5$-alkyl, $C_1$-$C_5$-alkoxy or $C_3$-$C_8$-cycloalkyl;
$C_2$-$C_{20}$-alkenyl optionally substituted by halogen, $C_1$-$C_5$-alkyl or $C_1$-$C_5$-alkoxy; $C_2$-$C_{20}$-alkynyl optionally substituted by halogen, $C_1$-$C_5$-alkyl or $C_1$-$C_5$-alkoxy; $C_3$-$C_8$-cycloalkyl optionally substituted by $C_1$-$C_5$-alkyl or $C_1$-$C_5$-alkoxy; $C_3$-$C_8$-heterocycloalkyl having one or more hetero atoms chosen from N, O and S and optionally substituted by $C_1$-$C_5$-alkyl or $C_1$-$C_5$-alkoxy; $C_6$-$C_{14}$-aryl-($C_1$-$C_{20}$)alkyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl, $C_1$-$C_5$-alkoxy, cyano, trifluoromethyl, carboxyl, carboxymethyl or carboxyethyl;
$C_6$-$C_{14}$-aryl optionally substituted by amino, hydroxyl, mercapto, halogen, $C_1$-$C_5$-alkyl, $C_1$-$C_5$-alkoxy;
$C_1$-$C_{13}$-heteroaryl having one or more hetero atoms chosen from N, O and S and optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$R^1$ and $R^2$, on the one hand, and $R^3$ and $R^4$, on the other hand, optionally forming with the nitrogen atom an n-membered ring (n between 3 and 8) optionally comprising one or more hetero atoms chosen from N, O and S and optionally being substituted by one of the following groups: amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;

$R^5$ is chosen from the following groups:
$C_1$-$C_{20}$-alkyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$-)-alkoxy, cyano, trifluoromethyl, carboxyl, carboxymethyl or carboxyethyl;
$C_2$-$C_{20}$-alkenyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_2$-$C_{20}$-alkynyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_3$-$C_8$-cycloalkyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_3$-$C_8$-heterocycloalkyl having one or more hetero atoms chosen from N, O and S and optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_6$-$C_{14}$-aryl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_1$-$C_{13}$-heteroaryl having one or more hetero atoms chosen from N, O and S and optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl;
$C_6$-$C_{14}$-aryl-($C_1$-$C_5$)-alkyl optionally substituted by amino, hydroxyl, mercapto, halogen, $C_1$-$C_5$-alkyl, $C_1$-$C_5$-alkoxy, $C_1$-$C_5$-alkylthio, $C_1$-$C_5$-alkylamino, $C_6$-$C_{14}$-aryl-oxy, $C_6$-$C_{14}$-aryl-($C_1$-$C_5$)-alkoxy, cyano, trifluoromethyl, carboxyl, carboxymethyl or carboxyethyl,
or a pharmaceutically usable derivative, solvate, salt or stereoisomer thereof,
said process comprising reacting a compound of the formula II:

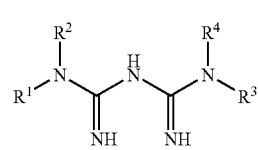

II in which $R^1$, $R^2$, $R^3$, $R^4$ are as defined above,
with a compound of the formula III:

$R^5$—CHO

III in which $R^5$ is as defined above,
in a polar solvent or solvant mixture in presence of an inorganic and/or organic base.

2. Process according to claim 1,
in which $R^1$, $R^2$ are independently from each other $C_1$-$C_{20}$-alkyl; $R^3$ and $R^4$ are H; and $R^5$ is $C_1$-$C_{20}$-alkyl (C1-C20).

3. Process according to claim 1,
in which $R^1$, $R^2$ are independently $C_1$-$C_6$-alkyl; $R^3$ and $R^4$ are H; and $R^5$ is $C_1$-$C_6$-alkyl.

4. Process according to claim 1,
in which $R^1$ and $R^2$ are methyl; $R^3$ and $R^4$ are H and $R^5$ is methyl.

5. Process according to claim 1, in which the base is chosen from alkali hydroxides, alkali carbonates and alkali alcoholates or organic bases chosen from triethyl amine, diisopropylethyl amine, pyridine, pyrrol, pyrrolidine, and piperidine, and any mixtures thereof.

6. Process according to claim 1, in which the solvent is chosen from water, methanol, ethanol, isopropanol, n-butanol, 2-butanol, i-butanol, t-butanol, N,N-dimethyl formamide and any mixtures thereof.

7. Process according to claim 1, in which the concentration of compound of formula III is from 1 equivalent to 10 equivalents based on the compound of the formula II.

8. Process according to claim 1, in which the base is present in an amount from 0.5 equivalents to 10 equivalents based on the compound of formula II.

9. Process according to claim 1, in which the compound of formula III is acetaldehyde.

10. Process according to claim 1, in which the reaction is performed under ambient pressure.

11. Process according to claim 1, in which the reaction is performed at room temperature.

* * * * *